United States Patent [19]

Drauz et al.

[11] Patent Number: 4,590,305

[45] Date of Patent: May 20, 1986

[54] PROCESS FOR THE SELECTIVE PRODUCTION OF DIHYDROXYBENZENES

[75] Inventors: Karlheinz Drauz, Freigericht; Axel Kleemann, Hanau, both of Fed. Rep. of Germany

[73] Assignee: Degussa Aktiengesellschaft, Frankfurt, Fed. Rep. of Germany

[21] Appl. No.: 587,651

[22] Filed: Mar. 8, 1984

[30] Foreign Application Priority Data

Mar. 11, 1983 [DE] Fed. Rep. of Germany ....... 3308763

[51] Int. Cl.$^4$ ............................................. C07C 37/00
[52] U.S. Cl. ..................... 568/771; 568/741; 568/798; 568/803
[58] Field of Search .............. 568/803, 771, 741, 798, 568/800, 803

[56] References Cited

U.S. PATENT DOCUMENTS 3,943,179  3/1976  Bost ..................................... 568/798

FOREIGN PATENT DOCUMENTS 2401758  9/1975  Fed. Rep. of Germany ...... 568/798
7312990  4/1974  Netherlands ........................ 568/771

OTHER PUBLICATIONS

Peroxide-Chemie GmbH, pp. 4-6 and 21-23, (1981).

Primary Examiner—Werren B. Lone
Attorney, Agent, or Firm—Cushman, Darby & Cushman

[57] ABSTRACT

The known nuclear hydroxylation of phenol or substituted phenols or phenol ethers with organic solutions of hydrogen peroxide in the presence of a catalyst is carried out in improved manner by employing both (1) a special, practically water free solution of hydrogen peroxide in an organic solvent which forms an azeotrope with water, which azeotrope boils below the boiling point of hydrogen peroxide, and (2) selenium dioxide as a catalyst. Through this, the nuclear hydroxylation is substantially simpler than previously. Besides, for the first time, it is possible to control the ortho to para ratio or the two ortho ratios to each other.

26 Claims, No Drawings

PROCESS FOR THE SELECTIVE PRODUCTION OF DIHYDROXYBENZENES

BACKGROUND OF THE INVENTION

The invention is directed to the hydroxylation of phenol, substituted phenols, and phenol ethers by nuclear hydroxylation of phenol with hydrogen peroxide with influence of the product selectivity in the production of ortho and para products.

Important hydroxybenzenes are derivatives of phenol, the napthols, and also derivatives of anthracene and phenanthrene. They are employed in the production of dyestuffs, in the production of synthetic resins, in photography, and for the production of important plant protectives. Thus, e.g., hydroquinone, the para hydroxylation product of phenol is used as a photo chemical; pyrocatechol, the corresponding ortho product for plant protection. For various areas of use, such as, e.g., as antioxidants, the dihydoxyphenols are mutually useful.

Their production, therefore, has long been the object of thorough investigations. The hydroxylation has been carried out both with hydrogen peroxide itself as well as with hydroperoxides, peroxides, or even per acids such as, e.g., performic acid or peracetic acid.

Nevertheless, hydrogen peroxide was preferred since it is the most readily available and since with percarboxylic acids, hydroperoxides and peroxides side reactions occur (European published application No. 0027593).

There was always present a catalyst in these hydroxylations. This catalyst can be a metalloid such as sulfur, selenium, tellurium, phosphorus arsenic, or antimony in elemental form (German OS-No. 2348957) or there can be used boron compounds (German Pat. No. 1543830).

Various processes operate with transition elements in the form of their ions (German OS No. 2162552), especially with iron ions (German OS No. 2162589 or German Pat. No. 2407398) or cobalt ions (German AS No. 2341743), or even with corresponding oxides (Milas U.S. Pat. No. 2,395,638).

Besides, there are employed strong acids such as sulfuric acid, sulfonic acids (German OS No. 2138735, German AS No. 2410742, German AS No. 2410758, German AS No. 2462967), or a mixture of sulfuric acid and phosphoric acid (German OS No. 2138735), there are also mentioned in the last named published application organic acids such as, inter alia, trichloroacetic acid or tartaric acid.

The already mentioned percarboxylic acids likewise serve as catalysts (French Pat. No. 1479354). In all of the mentioned catalysts, it is a matter with the catalysts being solid or liquid materials. Hydrogen peroxide, as preferred oxidation agent, for the most part is employed in aqueous solutions of various concentrations up to very high concentrations which have the danger of explosion; thus, the process according to German Pat. No. 2064497 operates with solutions which only contain 5 weight % water, but even at this highly concentrated hydrogen peroxide the yield of dihydroxy derivatives was only 70% and was reduced considerably according to the dilution of the hydrogen peroxide.

Additionally, in these and also in other processes, the operation must be carried out with a very large excess of the phenol to be hydroxylated in order in general to obtain the above-stated yield. If this excess is reduced, e.g., from 20 moles to 10 moles per mole of hydrogen peroxide, then the yield is reduced drastically despite the higher concentration of hydrogen peroxide.

However, as is known, this type of excess of a reactant, which must be recycled, requires additional industrial expense; above all in regard to the size of the apparatus employed.

Since care is always taken to avoid large excesses of one component as far as possible, there have been attempts to avoid employing aqueous solutions of hydrogen peroxide.

Thus, different solutions of hydrogen peroxide in organic solvents have already been used. For example, according to the process of German Pat. No. 2410758, there are preferably employed hydrogen peroxide solutions in derivatives of phosphoric acid or phosphonic acid, namely in the presence of a strong acid, such as sulfuric acid (100%) or fluorosulfonic acid.

However, these highly concentrated strong acids have the disadvantage that their separation from the rection mixture creates difficulties (German AS No. 2658943), above all since their concentration in the reaction mixture has a considerable influence on the length of the reaction.

The excess of phenol was indeed reduced somewhat in contrast to this in the process of German AS No. 2064497, but this did not outweigh the disadvantage of the strong acids.

An additional difficulty in the process of German Pat. No. 2410758 in the working up of the reaction mixture was produced by the presence of the water formed after the reaction with hydrogen peroxide.

Since the solvent for hydrogen peroxide employed in part is higher boiling than the phenols employed and this, especially with phenol itself, frequently forms an azeotrope with water whose boiling point is below that of the organic solvent, it was highly problematic that a trouble-free separation of the excess phenols from the reaction mixture could be attained.

Therefore, other ways were tried, first to manage without catalyst, i.e., above all without the strong acids. Since the catalysts above all were needed for the activation of hydrogen peroxide, the process of German AS No. 2658943 was operated with organic solutions of peracetic acid. An additional catalyst was not used.

Entirely apart from the fact that the mentioned process presupposes a complete plant for the production of an organic percarboxylic acid, which first is obtained from hydrogen peroxide and carboxylic acid, and thereupon is produced by extraction of this so-called "equilibrium acid" from its aqueous solution, it has been shown a stated good selectivity and good yield was only possible in the presence of additional peracid stabilizers (German OS No. 2364181; European OS No. 0027593). Furthermore, this selectivity, i.e., the ratio of ortho to para products, is controlled only according to the particular hydroxylation agent, e.g., percarboxylic acids and then can be influenced only by a change of the hydroxylation agent itself, and even then only to a moderate extent (German AS No. 2658943).

Using the same hydroxylation agent, but at different reaction temperatures, there occurs practically no change in the selectivity, see Table 1 of German Pat. No. 2364181.

Also, the addition of specific, chelate complex forming materials does not produce a remedy (German Pat. No. 2364181).

Likewise, changes of the reaction time have no influence on the selectivity (European OS No. 0027593).

From what has been said above, there is no known process either in the use of hydrogen peroxide itself or in the form of its per compounds, especially its percarboxylic acids, in spite of various additives as catalysts or stabilizers, which makes possible in a specific system on the one hand satisfactory yields and on the other hand also a regulation of the ratio of ortho to pure compounds or of ortho compounds to each other, as they occur in the substituted phenols obtained in the hydroxylation. In a given system, whose essential parameters were the particular hydroxylation agent and the particular catalyst, respectively, the particular catalysts, the selectivity represents a specific factor.

Since the ortho and para compounds or the ortho compound together as isomers are not identical in their properties and, therefore, indeed in part find different industrial uses, it became desirable to be able to influence the selectivity in the production of these two isomrs without great industrial expense, i.e., above all in a still further shifting of the equilibrium in favor of one of the two isomers, especially, e.g., of pyrocatechol, or e.g., of 4-methyl-pyrocatechol. Thereby, it is essential that the predetermined parameters of a system must not be changed.

SUMMARY OF THE INVENTION

It has now been found that the ratio of ortho to para products, respectively, ortho compounds to each other as they occur in the substituted phenols formed by hydroxylation can be influenced in the production of dihydroxybenzenes by nuclear hydroxylation of phenol or substituted phenols or their phenol ethers using only a single hydroxylation agent, namely hydrogen peroxide in an organic solvent in the presence of the same catalyst if the reaction is carried out in the presence of selenum dioxide and with a water-free solution of hydrogen peroxide, which preferably has a water content below 0.5 weight %, e.g 0.1%, and which is produced with an organic solvent which forms an azeotrope with water, which azeotrope has a boiling point below the boiling point of hydrogen peroxide, referred to normal pressure. As "water free" there is intended solutions which at most have up to 1 weight % of water.

As solvents, there can be used ethers such as dioxane, diisopropyl ether, methyl tert. butyl ether.

Preferred solvents are alkyl or cycloalkyl esters of saturated aliphatic carboxylic acids which contain 4–8 carbon atoms, e.g., alkyl alkanoates.

Especially suitable esters are those of acetic acid and propionic acid, above all n-propyl acetate or isopropyl acetate.

Other suitable esters include ethyl acetate, hexyl acetate, butyl acetate, sec. butyl acetate, amyl acetate, cyclohexyl acetate, cyclopentyl acetate, methyl propionate, ethyl propionate, propyl propionate, isopropyl propionate, butyl propionate, methyl butyrate, ethyl butyrate, n-propyl butyrate, ethyl valerate, ethyl hexanoate.

There can also be used mixtures of esters.

For the hydroxylation of preferred solutions are those with a weight ratio of about 1:4 to 2:1 $H_2O_2$/carboxylic acid ester.

This weight ratio is also attained in using less concentrated $H_2O_2$ solutions by distilling off from these solutions the carboxylic acid ester. The removal of the ester can be controlled by any desired value.

The mentioned solutions of hydrogen peroxide in alkyl or cycloalkyl esters are obtained according to the process of German OS No. 3225307.9, the entire disclosure of which is hereby incorporated by reference and relied upon.

The organic hydrogen peroxide solutions can be stabilized in customary manner, see Ullmann, Enzyklopadie der technischen Chemie, 4th Edition, Vol. 17, page 709, the entire disclosure of which is hereby incorporated by reference and relied upon. The concentration of the hydrogen peroxide in the solutions mentioned is, inter alia, 10 to 70 weight %. In each case, the solution mut be homogeneous.

The phenols employed for the nuclear hydroxylation are, in addition to phenol itself, substituted phenols as well as of phenol monoethers. Thus, there can be hydroxylated a lot of derivatives of phenol, e.g.,
2-chlorophenol, 3-chlorophenol, 4-chlorophenol,
2-fluorophenol, 3-fluorophenol, 4-fluorophenol,
4-carbomethoxyphenol, 2-methylphenol, 3-methylphenol,
4-methylphenol, 4-cyclohexylphenol, 2-cyclohexylphenol,
4-phenylphenol, 3-phenylphenol, 2-phenylphenol,
4-ethylphenol, 3-ethylphenol, 2-ethylphenol, 2-isopropylphenol, 3-isopropylphenol, 4-isopropylphenol,
4-tert.-butylphenol, phenylmethylether, 4-chlorophenylmethylether, 3-chlorophenylmethylether, 2-chlorophenylmethylether,
4'-methylphenylmethylether, 3'-methylphenylmethylether,
4-methoxy-1-phenylbenzene, ethyl-phenylether, isopropylphenylether, isopropyl-4'-methylphenylether, 1-hydroxynaphthalene,
2-hydroxynaphthalene, 1-methoxynaphthaline, 1-hydroxy-2-methylnaphthalene, 1-hydroxy-4-methylnaphthalene, 2-hydroxy-1-methylnaphthalene, 2-hydroxy-6-methylnaphthalene, 1-hydroxy-4-isopropylnaphthalene, 1-hydroxy-4-tert.-butyl-naphthalene,
1-hydroxy-6-phenylnaphthalene, 1-hydroxy-6-methoxynaphthalene, isopropyl-1-naphthyleter, isopropyl-2-naphthlether, phenyl-1-naphthylether, phenyl-2-naphthylether, 1-hydroxyanthracene,
1-methoxyanthracene, 2-hydroxyanthracene, 2-methoxyanthracene, 1-hydroxyphenanthrene, 3-hydroxyphenanthrene, 9-methoxyphenanthrene, 3-methoxyphenanthrene, 1-methoxyphenanthrene.

There can also be used halogen substituted phenols or alkoxy substituted phenols, e.g., 4-chlorophenol, 4-bromophenol, 4-fluorophenol, 3-chlorophenol, 2,4-dichlorophenol, 2-methoxyphenol, 4-ethoxyphenol.

The pressure is not critical for the reaction. Generally, the reaction is carried out at normal pressure.

The selenium dioxide is used in very small amounts, e.g., 0.0001 to 0.5 mole, preferably 0.0005 to 0.2 mole per mole of hydrogen peroxide.

The reaction generally occurs at 40 to 200° C., preferably at a temperature of 40° to 170° C.

Since selenium dioxide, the catalyst employed according to the invention and which is in solid, powdered form, or in certain cases, also in solution is very active in most cases after about 10 minutes, there is a reaction of around 85% or more, based on the hydrogen peroxide employed. The molar ratio of phenol of phenol derivative employed to hydrogen peroxide is between 5 to 20:1, preferably 5 to 15:1, very favorably at 7 to 15:1.

For the first time, it is possible by the process of the invention to control the ratio of ortho to para product, respectively, the ratio of two ortho products to each other using the same reaction system. For example, the theoretical ratio of ortho to para product in the hydroxylation of phenol is about 2:1. The ratio obtained according to the state of the art now is generally between the values of nearly 1:1 to about 3.5:1, and it must be emphasized that the breadth of deviation of one of the mentioned values in a specific system was very small and could not be pushed as desired in favor of one or the other of the isomers.

Exactly here is where the invention is employed.

It was completely unexpected that in the process of the invention the ratio of ortho to para products could be influenced simply by increasing the reaction time, see Examples 1 and 2.

In principle, an influencing of the corresponding isomers of the substituted phenols or phenol ethers, e.g., the cresols, likewise possible. Only here there the aim is more directed to producing the industrially more valuable product, such as, e.g., the corresponding 4-methyl pyrocatechol. This is obtained in extraordinary purity according to the process of the invention, see Example 3. The formation of isomers is almost completely suppressed in this case, i.e., the ortho position for the hydroxyl group of the substituted phenol is preferred to an extent not known previously.

The invention can comprise, consist essentially of, or consist of the stated steps with the recited materials.

The invention is explained in more detail in connection with the following examples.

In the tables in Examples 1 and 2, the abbreviations have the following meanings:
BC=pyrocatechol
HQ=hydroquinione
S $H_2O_2$=Yield of dihydric phenols based on the $H_2O_2$ reacted
%=mole %.

DETAILED DESCRIPTION

Example 1

65.8 grams (0.7 mole) of phenol were heated to 110° C. together with 0.011 gram (0.0001 mole) of selenium dioxide. There were quickly added to this vigorously stirred solution 12.2 grams of a 27.9 weight % solution of $H_2O_2$ in n-propyl acetate (=0.1 mole).

The temperature in the reaction mixture increased to a maximum of 147° C.

There were determined at the times stated in Table 1 the reaction of $H_2O_2$, the concentration and the ratio of dihydroxybenzenes and the selectivity in reference to $H_2O_2$ reacted.

TABLE 1

| Time (min) | Reaction $H_2O_2$ % | BC g | HQ g | BC/HQ | S $H_2O_2$ |
|---|---|---|---|---|---|
| 5 | 98 | 6.46 | 1.12 | 5.77 | 70.2 |
| 10 | 99.1 | 5.61 | 1.49 | 3.76 | 65.1 |
| 20 | 99.3 | 5.12 | 1.92 | 2.66 | 64.4 |
| 60 | 99.7 | 4.25 | 2.93 | 1.45 | 65.4 |
| 120 | 99.9 | 3.84 | 3.65 | 1.05 | 68.1 |

Example 2

941.1 grams (1.0 mole) of phenol were heated to 100° C. There were added to the stirred melt 0.033 (0.0003 mole) of selenium dioxide and 6.37 grams of a 53.4 weight % solution of $H_2O_2$ in n-propyl acetate (0.1 mole $H_2O_2$).

The temperature in the reaction solution increased to a maximum of 148° C.

There were determined at the times stated in Table 2 the reaction of $H_2O_2$, the concentration and the ratio of dihydroxybenzenes and the selectivity in reference to $H_2O_2$ reacted.

TABLE 2

| Time (min) | Reaction $H_2O_2$ % | BC g | HQ g | BC/HQ | S $H_2O_2$ |
|---|---|---|---|---|---|
| 5 | 83.4 | 6.27 | 1.24 | 5.06 | 81.8 |
| 10 | 85.8 | 5.75 | 1.30 | 4.42 | 74.6 |
| 20 | 88.1 | 5.68 | 1.73 | 3.28 | 76.4 |
| 60 | 92.0 | 5.12 | 2.44 | 2.10 | 74.6 |
| 120 | 96.0 | 3.90 | 3.39 | 1.15 | 68.9 |

Example 3

108.1 grams (1.0 mole) of p-cresol is heated to 100° C., then there were added to the stirred melt 0.011 gram (0.0001 mole) of $SeO_2$ and 12.2 grams of a 27.9 weight % solution of $H_2O_2$ in n-propyl acetate (0.1 mole $H_2O_2$).

The temperature increased to 149° C.

After 10 minutes, there was determined a hydrogen peroxide reaction of 98.8%. In the reaction mixture, there was formed 4-methyl pyrocatechol, which corresponds to a yield of 66.2 mole %, based on the $H_2O_2$ reacted. 4-methyl resorcinal was formed in an amount of 0.5 mole % (=traces, exactitude of analysis).

Example 4

108.1 grams (1.0 mole) of o-cresol were heated to 100° C. and reacted according to the conditions set forth in Example 2.

The temperature increased to 148° C.

After 10 minutes, there was determined a hydrogen peroxide reaction of 97.9%. In the reaction mixture, there were formed 7.37 grams (59.4 mmoles) of 3-methyl-pyrocatechol and 0.66 grams (5.3 mmoles) of 2-methyl-hydroquinone, which corresponds to a total yield of 66.1 mole % based on the $H_2O_2$ reacted.

The preparation of the reaction mixture is substantially simpler than the methods previously known.

Since the ester used as solvent according to the invention boils lower than the phenols which are converted, first there is distilled off an azeotrope between the ester and the water. The difficulties of a water-phenol separation, such as previously occurred, are eliminated. This is especially important since phenol is used in excess and must be returned again.

In the preparation, it is not absolutely necessary, because of the extremely low catalyst concentrations, to carry out a separation of the catalyst, for example, by neutralization, before a distillative separation. The crude reaction mixture is subjected directly to a distillation.

The entire disclosure of German priority application No. P. 3308763.6 is hereby incorporated by reference.

What is claimed is:

1. A process for the production of a dihydroxybenzene by nuclear hydroxylation of phenol, a substituted phenol, or a phenol ether with hydrogen peroxide in a substantially water-free organic solvent in the presence of a catalyst comprising reacting phenol with hydrogen peroxide in a solution in substantially water-free organic solvent which solvent forms an azeotrope with water, the boiling point of the azeotrope being below the boiling point of hydrogen peroxide, based on normal pressure, said reaction being carried out in the presence of selenium dioxide as a catalyst.

2. A process according to claim 1 wherein the water content of the solvent is below 0.5%.

3. A process according to claim 2 wherein the water content of the solvent is 0.1 percent by weight.

4. A process according to claim 1 wherein the solvent is an ether or an alkyl or cycloalkyl ester of a saturated, aliphatic carboxylic acid, which ester contains a total of 4–8 carbon atoms.

5. A process according to claim 4 wherein the solvent is an alkyl or cycloalkyl ester of a saturated aliphatic carboxylic acid, which ester contains a total of 4–8 carbon atoms.

6. A process according to claim 5 wherein the solvent is an alkyl alkanoate.

7. A process according to claim 4 wherein the solvent is an ester of acetic acid or propionic acid.

8. A process according to claim 7 wherein the hydrogen peroxide is employed as a solution in n-propyl acetate or isopropyl acetate.

9. A process according to claim 8 wherein there is employed selenium dioxide in an amount of 0.0001 to 0.5 mole per mole of hydrogen peroxide.

10. A process according to claim 1 wherein there is employed sulfur dioxide in an amount of 0.0001 to 0.5 mole per mole of hydrogen peroxide.

11. A process according to claim 10 wherein there is employed 0.0005 to 0.2 mole of selenium dioxide per mole of hydrogen peroxide.

12. A process according to claim 11 wherein the molar ratio of phenol to hydrogen peroxide is from 7 to 15:1.

13. A process according to claim 1 wherein the molar ratio of phenol to hydrogen peroxide is from 5 to 20:1.

14. A process according to claim 1 wherein the starting compound is phenol, an alkyl phenol, an arylphenol, a halophenol, an alkoxyphenol, a phenyl alkyl ether, an alkyl phenol alkyl ether, a naphthol, a hydroxyanthracene, or a hydroxyphenanthrene.

15. A process according to claim 14 wherein the starting compound is phenol, o-cresol, or p-cresol.

16. A process according to claim 15 wherein the starting compound is phenol.

17. A process according to claim 16 wherein the reaction is stopped before the ratio of pyrocatechol to hydroquinone drops below about 2.66:1.

18. A process according to claim 16 wherein the reaction is stopped before the ratio of pyrocatechol to hydroquinone drops below about 3.76:1.

19. A process according to claim 16 wherein the reaction is stopped before the ratio of pyrocatechol to hydroquinone drops below about 5.77:1.

20. A process according to claim 1 wherein the reaction is continued for at least about 60 minutes.

21. A process according to claim 1 wherein the reaction is continued for not over about 20 minutes.

22. A process according to claim 1 wherein the reaction is continued for not over about 10 minutes.

23. A process according to claim 1 wherein the reaction is continued for not over about 5 minutes.

24. A process according to claim 1 wherein the temperature is 40° to 200° C.

25. A process according to claim 24 wherein the temperature is 40° to 170° C.

26. A process according to claim 24 whrein the solvent is an ether or an alkyl or cycloalkyl ester of a saturated, aliphatic carboxylic acid, which ester contains a total of 4–8 carbon atoms.

* * * * *